(12) United States Patent
Rosen et al.

(10) Patent No.: US 12,207,941 B2
(45) Date of Patent: Jan. 28, 2025

(54) PSYCHOPHYSICAL METHOD TO CHARACTERIZE VISUAL SYMPTOMS

(71) Applicant: AMO Groningen B.V., Groningen (NL)

(72) Inventors: Robert Rosen, Groningen (NL); Carmen Canovas Vidal, Groningen (NL)

(73) Assignee: AMO Groningen B.V., Groningen (NL)

( * ) Notice: Subject to any disclaimer, the term of this patent is extended or adjusted under 35 U.S.C. 154(b) by 1031 days.

(21) Appl. No.: 16/271,648

(22) Filed: Feb. 8, 2019

(65) Prior Publication Data
US 2019/0239803 A1    Aug. 8, 2019

Related U.S. Application Data

(60) Provisional application No. 62/628,171, filed on Feb. 8, 2018.

(51) Int. Cl.
*A61B 5/00*    (2006.01)
*A61B 3/02*    (2006.01)
(Continued)

(52) U.S. Cl.
CPC .............. *A61B 5/4851* (2013.01); *A61B 3/02* (2013.01); *A61B 5/16* (2013.01); *A61B 5/7264* (2013.01); *A61B 5/7282* (2013.01); *A61B 5/742* (2013.01); *A61F 2/16* (2013.01); *A61B 3/032* (2013.01); *A61B 3/06* (2013.01)

(58) Field of Classification Search
CPC ........... A61B 3/02; A61B 3/022; A61B 3/032; A61B 3/06; A61B 5/7264; A61B 5/2782; A61F 2/16
See application file for complete search history.

(56) References Cited

U.S. PATENT DOCUMENTS

| | | | |
|---|---|---|---|
| 5,065,767 A | * | 11/1991 | Maddess ................... A61B 3/06 351/239 |
| 6,460,997 B1 | | 10/2002 | Frey et al. |
| (Continued) | | | |

FOREIGN PATENT DOCUMENTS

| | | |
|---|---|---|
| EP | 0538126 B1 | 9/1996 |
| EP | 3059575 A1 | 8/2016 |
| (Continued) | | |

OTHER PUBLICATIONS

"Lesmes, L.A., Lu, Z.L., Baek, J., Albright, T. Bayesian adaptive estimation of the contrast sensitivity function: The quick CSF method. Mar. 2010. Journal of Vision. vol. 10. Issue 3. pp. 1-10." (Year: 2010).*

(Continued)

*Primary Examiner* — Benjamin S Melhus
*Assistant Examiner* — Severo Antonio P Lopez
(74) *Attorney, Agent, or Firm* — Roy Kim (57) ABSTRACT

A psychophysical method, system, and apparatuses to characterize visual symptoms. A method may include presenting one or more stimuli to a patient indicating one or more visual symptoms. The patient may produce one or more responses to the stimuli. A determination of a measure of visual symptoms of the patient may be made utilizing a Bayesian method based on the responses.

8 Claims, 4 Drawing Sheets

(51) Int. Cl.

| | |
|---|---|
| A61B 3/032 | (2006.01) |
| A61B 3/06 | (2006.01) |
| A61B 5/16 | (2006.01) |
| A61F 2/16 | (2006.01) |

(56) References Cited

U.S. PATENT DOCUMENTS

| | | | |
|---|---|---|---|
| 6,497,483 | B2 | 12/2002 | Frey et al. |
| 6,575,572 | B2 | 6/2003 | Lai et al. |
| 6,609,793 | B2 | 8/2003 | Norrby et al. |
| 7,659,971 | B2 | 2/2010 | Warden et al. |
| 7,938,538 | B2 | 5/2011 | Lu et al. |
| 7,944,553 | B1 | 5/2011 | Simpson et al. |
| 7,969,585 | B2 | 6/2011 | Neal et al. |
| 9,700,201 | B2 | 7/2017 | Bex et al. |
| 10,448,819 | B2 | 10/2019 | Weeber |
| 2003/0033013 | A1 | 2/2003 | Callahan et al. |
| 2005/0024647 | A1 | 2/2005 | Montgomery |
| 2006/0203198 | A1 | 9/2006 | Liang |
| 2006/0244906 | A1 | 11/2006 | Piers et al. |
| 2006/0279699 | A1 | 12/2006 | Liang |
| 2006/0279700 | A1 | 12/2006 | Liang |
| 2008/0033546 | A1 | 2/2008 | Liang |
| 2009/0000628 | A1 | 1/2009 | Somani et al. |
| 2010/0097569 | A1 | 4/2010 | Weeber et al. |
| 2011/0211163 | A1* | 9/2011 | Meuse ............. A61B 3/02 351/239 |
| 2012/0238904 | A1 | 9/2012 | Manns et al. |
| 2012/0296422 | A1 | 11/2012 | Weeber |
| 2013/0314669 | A1 | 11/2013 | Levin et al. |
| 2014/0176904 | A1 | 6/2014 | Lai |
| 2015/0379348 | A1 | 12/2015 | Whritenor et al. |

FOREIGN PATENT DOCUMENTS

| | | | |
|---|---|---|---|
| GB | 2433782 | A | 7/2007 |
| GB | 2488802 | A | 9/2012 |
| WO | 0189424 | A1 | 11/2001 |
| WO | 02074210 | A2 | 9/2002 |
| WO | 2004079637 | A1 | 9/2004 |
| WO | 2005079546 | A2 | 9/2005 |
| WO | 2007142981 | A2 | 12/2007 |
| WO | 2010028654 | A1 | 3/2010 |
| WO | 2012166797 | A1 | 12/2012 |
| WO | 2016032397 | A1 | 3/2016 |
| WO | 2016087914 | A1 | 6/2016 |

OTHER PUBLICATIONS

"Abrahamsson, M., Sjostrand, J. Impairment of contrast sensitivity function (CSF) as a measure of disability glare. Jul. 1986. Investigative Opthamology & Visual Science. vol. 27. Issue 7. pp. 1131-1136." (Year: 1986).*

"Buckhurst, P.J., Naroo, S.A., Davies, L.N., Shah, S., Drew, T., Wolffsohn, J.S. Assessment of dysphotopsia in pseudophakic subjects with multifocal intraocular lenses. Jun. 19, 2017. BMJ Open Opthalmology. vol. 1. pp. 1-6" (Year: 2017).*

"Sen, H.N., Sarikkola, A., Uusitalo, R.J., Laatikainen, L. Quality of vision after AMO Array multifocal intraocular lens implantation. Dec. 2004. Journal of Cataract & Refractive Surgery. vol. 30, Issue 12. pp. 2483-2493" (Year: 2004).*

"McAlinden, C. et al. The Development of an Instrument to Measure Quality of Vision: The Quality of Vision (QoV) Questionnaire. Nov. 2010. Investigative Ophthalmology & Visual Science. vol. 51, Issue 11. pp. 5537-5545" (Year: 2010).*

Beer J.M., et al., "Lasers' Spectral and Temporal Profile Can Affect Visual Glare Disability," Aviation, Space, and Environmental Medicine, Dec. 2012, vol. 83 (12), pp. 1135-1144.

Javitt J.C., et al., "Validity and Reliability of the Cataract TyPE Spec: an Instrument For Measuring Outcomes of Cataract Extraction," American Journal of Ophthalmology, Aug. 2003, vol. 136 (2), pp. 285-290.

Johnson C.A., "Psychophysical Factors that Have Been Applied to Clinical Perimetry," Vision Research, Sep. 2013, vol. 90, pp. 25-31.

Lesmes L.A., et al., "Bayesian Adaptive Estimation of the Contrast Sensitivity Function: the Quick CSF Method," Journal of Vision, Mar. 2010, vol. 10 (3) 17, pp. 1-21.

Vitale S., et al., "The Refractive Status and Vision Profile: A Questionnaire to Measure Vision-Related Quality of Life in Persons with Refractive Error," Ophthalmology, Aug. 2000, vol. 107 (8), pp. 1529-1539.

Abrahamsson M., et al., "Impairment of Contrast Sensitivity Function (CSF) as a Measure of Disability Glare," Investigative Ophthalmology & Visual Science, Jul. 1986, vol. 27 (7), pp. 1131-1136.

Aslam, T.M., et al., "Development of a Forced Choice Photographic Questionnaire For Photic Phenomena and Its Testing—Repeatability, Reliability and Validity," Ophthalmologica, Nov.-Dec. 2004, vol. 218 (6), pp. 402-410.

International Search Report for Application No. PCT/EP2019/053204, mailed Jun. 24, 2019, 16 pages.

Ortiz, C., et al., "Quantification and Monitoring of Visual Disturbances for patients with cataracts using Halo v1.0 software," Department of Optics, Laboratory of Vision Sciences and Applications, University of Granada, IWBBIO 2013, Mar. 20, 2013, XP055596332, Proceedings, 8 Pages.

Calatayud A., et al., "Imaging Quality of Multifocal Intraocular Lenses: Automated Assessment Setup," Ophthalmic and Physiological Optics, Jul. 2013, vol. 33 (4), pp. 420-426.

Fernandez E.J., et al., "Adaptive Optics Visual Simulator," Journal of Refractive Surgery, 2002, vol. 18 (5), pp. S634-S638.

Guirao A., et al., "Corneal Wave Aberration from Videokeratography: Accuracy And Limitations of the Procedure," Journal of the Optical Society of America, 2000, vol. 17 (6), pp. 955-965.

Jaeken B., et al., "Peripheral Aberrations in the Human Eye for Different Wavelengths: Off-Axis Chromatic Aberration," Journal of the Optical Society of America A, Sep. 2011, vol. 28 (9), pp. 1871-1879.

Jendritza B.B., et al., "Wavefront-Guided Excimer Laser Vision Correction after Multifocal IOL Implantation," Journal of Refractive Surgery, Mar. 2008, vol. 24 (3), pp. 274-279.

Morlock, R., et al., "Patient-Reported Spectacle Independence Questionnaire (PRSIQ): Development and Validation,"American Journal of Ophthalmology, Jun. 2017, vol. 178, pp. 101-114.

Rosen R., et al., "A Bayesian Method Using through Focus Visual Acuity to Predict Rates of Spectacle Wear for Pseudophakic patients," Investigative Ophthalmology & Visual Science, Jul. 2018, vol. 59 (9), pp. 1075, ARVO Annual Meeting Abstract, Retrieved from the Internet: (URL: https://iovs.arvojournals.org/article.aspx?articleid=2693341&resultClick=1).

Weeber H.A., et al., "Influence of Corneal Aberrations on Dysphotopsia with Multifocal IOLs," ARVO, 2011, Abstract.

Weeber H.A., et al., "Influence of Corneal Aberrations on Dysphotopsia with Multifocal IOLs," RD3115, 2011.

Weeber H.A., et al., "Optical and Visual Performance of Patient Populations Implanted with Monofocal and Multifocal IOLs in the Presence of Defocus," Investigative Ophthalmology & Visual Science, 2010, vol. 51, E-Abstract 5751.

Weeber H.A., et al., "Population-based Visual Acuity in the Presence of Defocus Well Predicted By Classical Theory," Journal of Biomedical Optics, 2010, vol. 15 (4), pp. 040509.

Weeber H.A., et al., "Theoretical Performance of Intraocular Lenses Correcting Both Spherical and Chromatic Aberration," Journal of Refractive Surgery, 2012, vol. 28 (1), pp. 48-52.

Kontsevich L.L., et al., "Bayesian Adaptive Estimation of Psychometric Slope and Threshold," Vision Research, Aug. 1999, vol. 39 (16), pp. 2729-2737.

* cited by examiner

PSYCHOPHYSICAL METHOD TO CHARACTERIZE VISUAL SYMPTOMS

CROSS-REFERENCE TO RELATED APPLICATIONS

This application claims the benefit under 35 U.S.C. § 119(e) of U.S. Provisional Patent Application No. 62/628,171, filed Feb. 8, 2018, which is incorporated herein by reference in its entirety.

BACKGROUND

Intraocular lens designs may suffer from various visual symptoms including glare and halos. Visual symptoms may be challenging to characterize clinically, and there may be a great deal of variability in patient responses. Thus, the visual symptom characteristics of an intraocular lens design can be uncertain, even after clinical studies. Further, there may be a great deal of subjective bias, because visual symptoms mostly rely on self-reported questionnaires. This may create uncertainty when it comes to visual symptom performance of intraocular lenses.

A common way to assess visual symptoms of lenses is to have patients respond to a questionnaire. Complaints about visual symptoms are gathered either through spontaneous mention by patients, or by specifically asking them about the phenomenon. Such sampling techniques are statistically difficult due to the low granularity of answers (typically just a few options of intensity), the subjectivity of evaluation resulting in a bias, and the relatively low numbers of individuals complaining.

The prior assessment techniques accordingly are difficult and unreliable.

SUMMARY

Disclosed herein are methods, systems, and apparatuses intended to improve measurement of visual symptoms of a patient. Such methods may include a psychophysical method to characterize visual symptoms. The methods may utilize Bayesian methods to improve measurement of visual symptoms.

A method according to an embodiment of the disclosure may include presenting a first stimulus to a patient indicating one or more visual symptoms. The method may include receiving a first response to the first stimulus by the patient. The method may include presenting a second stimulus to a patient indicating one or more visual symptoms. The method may include receiving a second response to the second stimulus by the patient. The method may include determining a measure of visual symptoms of the patient utilizing a Bayesian method based on the first response and the second response. The method may include presenting at least ten, or least 30, or at least 50, or a greater number of stimuli to the patient indicating one or more visual symptoms, and receiving responses to the respective stimuli by the patient, and determining a measure of visual symptoms of the patient utilizing a Bayesian method based on the responses. The stimuli and responses may be iteratively provided and received to produce a desired measurement of visual symptoms (e.g., iteratively performed at least 10, 20, 30, 50, 100, or more, times).

A method according to an embodiment of the disclosure may include presenting a stimulus to a patient indicating one or more visual symptoms. The method may include receiving a response to the stimulus by the patient. The method may include updating a prior probability of visual symptoms for the patient based on the response. The method may include determining a measure of visual symptoms of the patient based on the updated prior probability.

A method according to an embodiment of the disclosure may include presenting a first stimulus to a patient indicating one or more visual symptoms. The method may include receiving a first response to the first stimulus by the patient. The method may include determining, based on the first response, a second stimulus to present to the patient to reduce the expectation value of entropy for patient response. The method may include presenting the second stimulus to a patient indicting one or more visual symptoms. The method may include receiving a second response to the second stimulus by the patient. The method may include determining a measure of visual symptoms of the patient, based on the first response and the second response. This may be repeated at least 10, 20, 30, 50, 100, or more, times as desired.

BRIEF DESCRIPTION OF THE DRAWINGS

Features and advantages of the systems, apparatuses, and methods as disclosed herein will become appreciated as the same become better understood with reference to the specification, claims, and appended drawings wherein:

DETAILED DESCRIPTION

Figure 1:
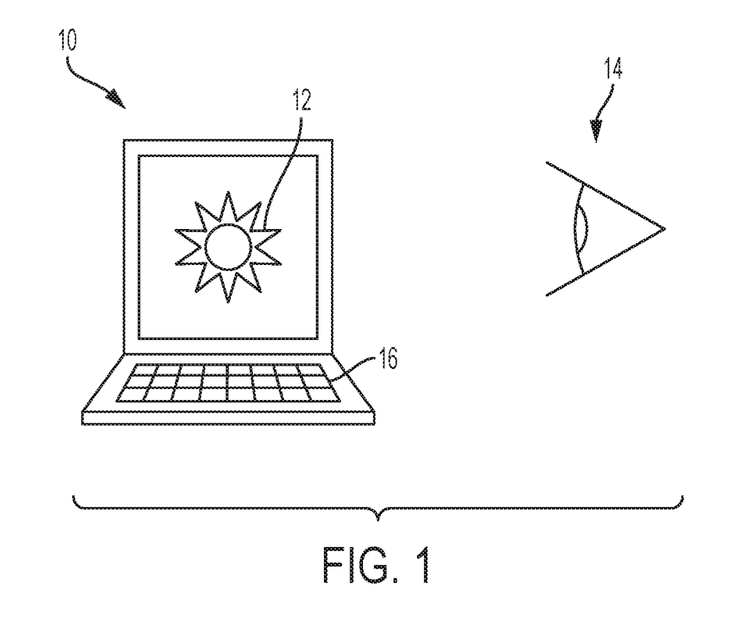
FIG. 1 illustrates a schematic view of a system according to an embodiment of the present disclosure.

FIG. 1 illustrates a system including a display 10. The display 10 may comprise a computer screen, as shown in FIG. 1. In other embodiments, other forms of displays, such as mobile device displays or other forms of display screens may be utilized.

The display 10 may be configured to present a stimulus 12 to a individual who may be a patient 14. In FIG. 1 the patient 14 is represented with an eye, which would view the stimulus 12 on the display 10.

The stimulus 12 may indicate one or more visual symptoms to a patient 14. The stimulus 12 may comprise an image, as shown in FIG. 1. In FIG. 1 an image of visual symptoms comprising glare and halo is presented to the patient 14. The stimulus 12 is presented for response by the patient 14. The response indicates the visual symptoms of the patient 14. The stimulus 12 may be designed to elicit an indication of visual symptoms from the patient 14. The response may indicate the presence of visual symptoms in the patient, such as glare, halo, or other forms of visual symptoms. For example, the response may indicate the degree to which the patient 14 suffers from visual symptoms. The response may indicate whether the patient 14 has visual symptoms that are better or worse that the visual symptoms indicated by the stimulus 12. The response accordingly may comprise a binary response (e.g., yes/no) by the patient 14.

In certain embodiments, the response may indicate a quantitative amount or score to which the patient 14 has visual symptoms.

The system may include an input device for the patient 14 to produce the response to the stimulus. In FIG. 1 the input device 16 comprises a keyboard. In other embodiments, other forms of input devices such as touchscreens, keypads, buttons, microphones or other input devices, may be utilized.

Figure 2:
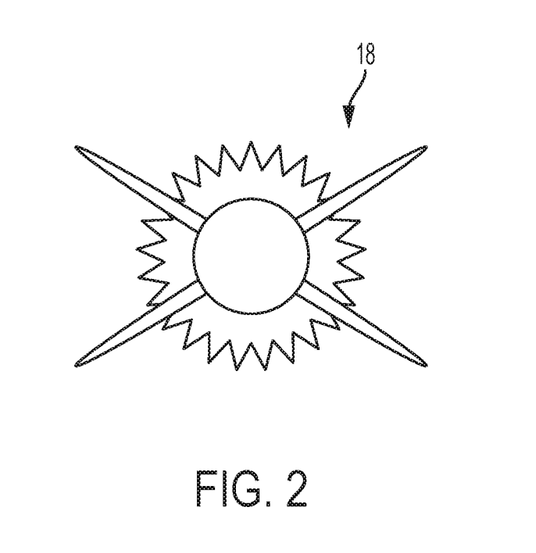
FIG. 2 illustrates a stimulus according to an embodiment of the present disclosure.

FIG. 2 disclose a stimulus 18 in form of an image. The image comprises an image of glare and halo. The image indicates one or more visual symptoms to the patient 14. The glare and halo may be of a kind produced by an intraocular lens. The patient 14 may provide a response indicating whether the visual symptoms of the patient 14 are better or worse than the stimulus 18. For example, the patient may press a button or provide another form of input if the visual symptoms of the patient 14 are at least as bad as the stimulus 18. The patient may press a different button or provide another form of input if the visual symptoms of the patient are not at least as bad as the stimulus 18. Such a response is a binary response by the patient (e.g., whether the experienced visual symptoms are at least as bad as the image shown). In other embodiments, the patient may provide an input that the symptoms are entirely different than the shown image. In other embodiments, the patient may press a button stating the glare is 30% worse than the shown image. The patient may provide varied forms of responses to the stimulus. However, a binary response is preferred.

Figure 3:
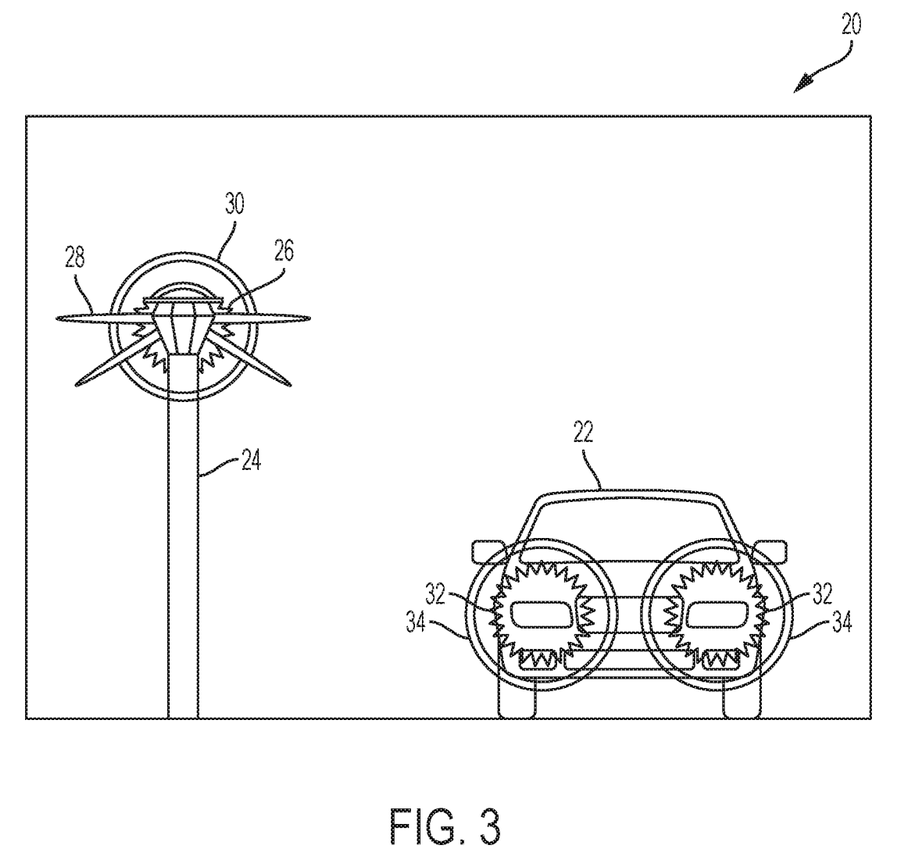
FIG. 3 illustrates a stimulus according to an embodiment of the present disclosure.

FIG. 3 discloses a stimulus 20 in the form of an image of a scene. The scene comprises an automobile 22 next to a street lamp 24. The street lamp 24 is shown to produce glare 26. The street lamp also shows two types of halos—a starburst 28 type halo and a small ring 30 type halo. The head lights of the automobile 22 are also shown to produce glare 32. The head lights are shown to produce large halos 34. A variety of forms of stimuli may be provided to the patient 14. For example, a combination of different size, type, and intensity of halos may be provided. Multiple dimensions of visual symptoms may be shown. This may be pertinent if the street lamp and automobile in reality have characteristics of a light source that are different (e.g., in wavelength and baseline intensity).

The patient may provide a response to the stimulus 20 indicating whether the visual symptoms of the patient 14 are better or worse than the stimulus 20. Such a response may be a binary response. The patient may provide a single preference decision based on the whole image, and may provide a single response based on the image. The total quality of the visual symptoms in the image may be evaluated. In one embodiment, the patient may provide responses for individual features of the image separately (e.g., the street lamp may be responded to separate from the automobile).

The use of the scene in FIG. 3 may enhance the ability of the patient 14 to accurately determine whether visual symptoms match those of the scene. The patient's 14 memory may be improved through use of the scene. The visual symptoms seen with the patients may be real, and the stimuli presented on the test screen may match the actual visual symptoms completely.

The stimulus may be provided in a manner that elicits a binary response from the patient. For example, the stimulus may ask "IS THE PRESENTED STIMULI STRONGER OR WEAKER THAN WHAT YOU EXPERIENCE DAILY?," or "WOULD YOU BE BOTHERED BY VISUAL SYMPTOMS AS PRESENTED BY THIS IMAGE?" In one embodiment, a stimulus in the form of an actual physical light source may be presented to the patient. The patient may then be asked to view another stimulus on a display screen or the like and asked to compare the visual symptoms caused by the physical light source and the stimulus on the display screen. The patient may be asked "COMPARED TO THE EXPERIMENTAL SETUP TO THE SIDE, WHICH HAS A LIGHT (thus inducing the visual symptom), IS THE PICTURE (on the screen) SHOWING STRONGER OR WEAKER VISUAL SYMPTOMS FOR YOU?" In one embodiment, the stimulus may comprise a physical light source alone and the patient may be asked "IN THE PRESENCE OF THIS GLARE SOURCE, DO YOU EXPERIENCE DISTURBING VISUAL SYMPTOMS?" Binary responses may be provided by the patient.

The response provided by the patient 14 may be utilized in a Bayesian method. The Bayesian method may be utilized to determine a measure of visual symptoms of the patient. Bayesian methods are utilized to produce a posterior probability based on a likelihood and a prior probability. The posterior probability may be proportional to the likelihood and the prior probability. The Bayesian method may be used to determine a measure of visual symptoms based on evidence (the response or responses to the stimulus or stimuli). This is a process of Bayesian inference.

The prior probability, at first, comprises an initial probability. The initial probability may comprise an initial measure of the patient 14 having certain visual symptoms. In one embodiment, the initial probability may be relatively flat for the patient 14. In one embodiment, an initial probability may be determined for the patient 14 based on information regarding the patient. For example, the initial probability may be determined based on whether the patient belongs to certain demographic groups. The demographic groups may comprise a comparison population of interest, such as patients that have intraocular lenses (monofocal or multifocal), or patients that have cataracts, or other demographic groups. The patient may be matched to the initial probability for patients in the same demographic groups. In one embodiment, the initial probability may be determined to comprise the initial probability for a typical monofocal patient. The initial probability may be determined by being selected from a set of initial probabilities, which may be predetermined.

The parameters of the Bayesian method may be set as desired. In one embodiment, the parameters may be set to correspond to visual symptoms of a patient having an intraocular lens implanted in the patient's eye. The parameters may each indicate a characteristic of a visual symptom (e.g., one or more or a type, size, or intensity of halo or glare). For example, in one embodiment, four parameters may be utilized. The four parameters may correspond to a type of halo, a size of the halo, an intensity of the halo, and glare (with glare comprising a single intensity parameter (e.g., veiling luminance)). The type of halo may correspond to the shape of the halo, such as starbursts, small rings, or large rings. In other embodiments, a greater or lesser number of parameters may be utilized. For example, in one embodiment, five parameters may be utilized (a type of halo, a size of the halo, an intensity of the halo, an intensity of glare, and angle of glare). In one embodiment eight parameters may be used. The eight parameters may be used in which a combination of two types of halos are used, in combination with glare (e.g., size and intensity of halo type 1, size and intensity of halo type 2, and size and intensity of glare). In one embodiment, additional or other parameters such as width of halo rings, or repetition or halo rings may be utilized. The type and number of parameters may be determined based on the desired measure of patient visual symptoms to be obtained.

The initial probability for the patient 14 may comprise a probability for each combination of parameters. The initial probability may correspond to the likelihood of the patient 14 experiencing visual symptoms that are at least that bad in each of the different dimensions. This probability may comprise a probability density function. The probability density function may be initially flat. In one embodiment, the probability distribution function may be set to a comparison group of interest in the manner discussed previously.

The response to the stimulus is provided by the patient 14. The stimulus may be selected such that the parameters are varied across different dimensions. The patient 14 may provide the response to the stimulus, which may be referred to as the "first stimulus," that indicates whether the visual symptoms of the patient 14 are at least as bad as the first stimulus. A binary response may be provided.

Upon receipt of the response from the patient 14, which may be referred to as the "first response," the system may update the prior probability (which is the initial probability in this example) based on the response. The prior probability may be updated in a Bayesian method, based on the response provided by the patient 14. The initial probability is now updated to comprise the prior probability based on the first response.

The system may determine a "second stimulus" to present to the patient 14 based on the "first response." The system may determine a second stimulus to reduce the expectation value of entropy for a patient response. For example, if the first stimulus were the image shown in FIG. 3, and the patient 14 provided a first response that the patient's visual symptoms were not at least as bad as the first stimulus, then the second stimulus would be chosen to comprise an image with lesser glare and halos than shown in FIG. 3 (because the patient indicated that the symptoms were not as bad). In this example, the test would be inefficient if the second stimulus comprised a scene with worse glare and halos than shown in FIG. 3 (because the patient would simply continue to indicate that the patient's symptoms were not as bad). All of the parameters may be updated and potentially changed in the next stimulus presentation. The algorithm accordingly may make intelligent guesses as to the threshold values associated with different combinations of parameters, without having to vary them one by one.

The expectation value of entropy for a patient response may be reduced as a probability density function may be a multi-dimensional matrix with a probability associated with each possible combination of thresholds. If a response is associated with a certain combination of stimuli, the whole probability density function may be updated. For a given stimuli, the probability of a binary response (e.g., yes/no) may be estimated. For a given probability density function, its entropy may be calculated. The entropy is the spread of the probability density function (e.g., lowest entropy is a single combination of parameters having value 1, all others have 0; highest entropy is if all of the combinations of parameters have the same (very low) probability). For each potential stimulus shown, the estimated entropy that would result from showing the stimulus may be calculated. The stimulus that will result in the greatest reduction of entropy may thus be determined and provided to the patient. As such, a probability density function of combinations of thresholds of the plurality of parameters may be calculated, and selection of stimuli for presentation to the patient that will minimize an entropy of the probability density function may be performed. The minimization may be the fastest or most efficient minimization.

Figure 4A:
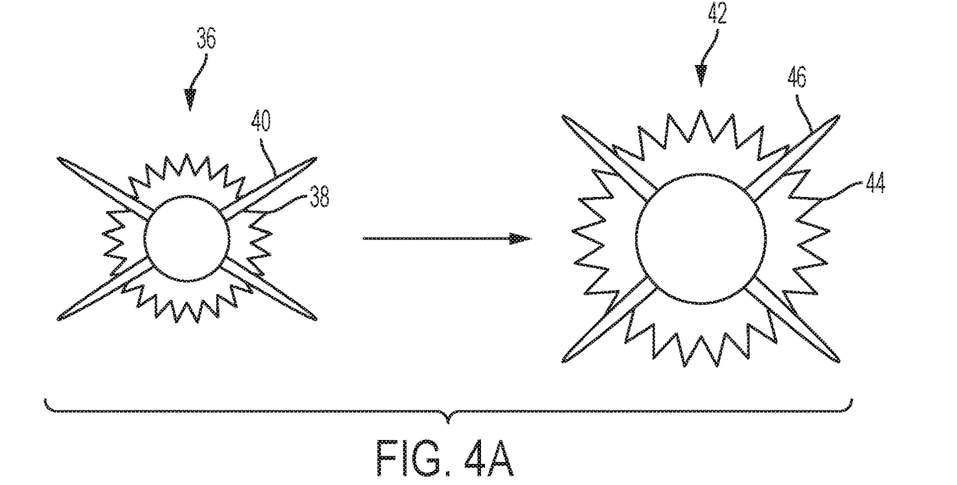
FIGS. 4A, 4B, and 4C each illustrate a representation of a successive stimulus according to an embodiment of the present disclosure.

FIG. 4A illustrates a representation of determination of the "second stimulus." A prior or "first" stimulus 36 is shown as a combination of glare 38 and halo 40. The halo 40 may be a starburst type. The patient 14 may provide a response that his or her visual symptoms are at least as bad as the stimulus 36. A binary response may be provided for the whole image. If the patient indicates visual symptoms are at least as bad, then a successive or "second" stimulus 42 may be provided with greater glare 44 and halo 46.

Figure 4B:
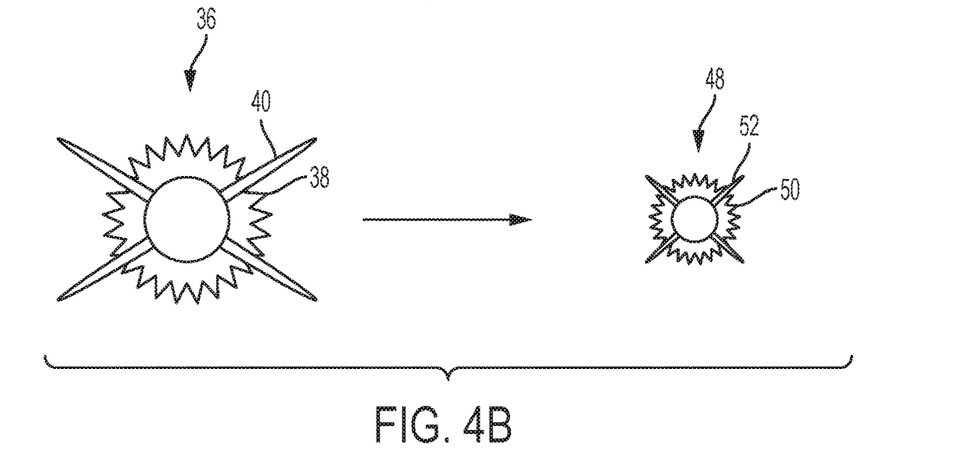

FIG. 4B illustrates a similar representation of determination of the "second stimulus." The patient 14 may provide a response that his or her visual symptoms are not at least as bad as the stimulus 36. If the patient indicates visual symptoms are not at least as bad, then a successive or "second" stimulus 48 may be provided with lesser glare 50 and halo 52.

Figure 4C:
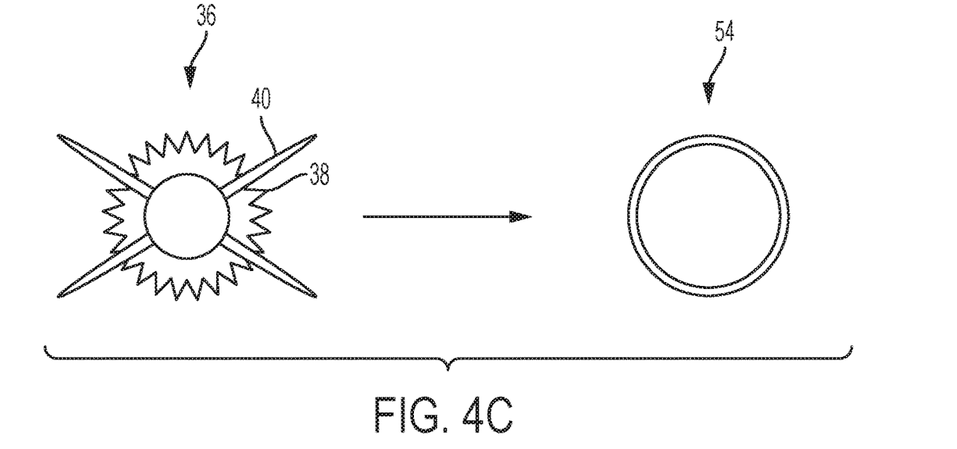

FIG. 4C illustrates another representation of determination of the "second stimulus." The patient 14 may provide a response that his or her visual symptoms are either not at least as bad as the stimulus 36, or are as bad. The system may determine to test another parameter, and may provide a second stimulus 54 of only a large ring halo to test whether the patient's visual symptoms are at least as bad as the stimulus 54. Preferably, however, some aspect of all parameters will be present in each stimulus present (although if the threshold is low, some may be so low that they are not visible). Upon receipt of the response to the second stimulus from the patient 14, which may be referred to as the "second response," the system may update the prior probability (determined from the first response) based on the second response. The prior probability may be updated in a Bayesian method, based on the second response provided by the patient 14. The prior probability is now based on the first response and the second response.

The determination of the next, or "third stimulus," may proceed in a similar manner as described above regarding the determination the "second stimulus." The third response may be provided to the third stimulus by the patient. The prior probability may be updated in a similar manner as with the second stimulus, such that the prior probability is based on the third response, the second response, and the first response. Under the Bayesian method, the prior probability remains based on the first response and the second response even though the third response is also utilized.

The determination of successive stimuli, and responses by the patient, may continue iteratively. The determination of the prior probabilities may also continue iteratively. The process may continue for as many steps as desired to produce a desired measure of the visual symptoms of the patient. The number of iterations may comprise more than 10, 20, 30, 40, 50, 100, or more steps, as desired. In one embodiment, the process may stop when a predetermined certainty threshold is reached. This may be based on calculation of the entropy of the probability density matrix. At each step, a selection of stimuli for presentation to the patient that will minimize an entropy of the probability density function may be determined and the corresponding stimulus may be provided to the patient.

The calculation of the prior probabilities may occur at each step, upon receipt of the response to the successive stimulus from the patient 14. In one embodiment, the calculation of the prior probabilities may occur at one time at the end of all the testing steps.

The testing may result in determination of a measure of visual symptoms of the patient 14. The measure may be provided in many forms. The measure may comprise a determination that the visual symptoms of the patient 14 exceed a threshold. For example, the measure may be a finding that the patient exceeds a threshold for severe halos. An output may be provided, such as a textual output that the patient 14 "has severe halos." A binary output may be provided. For example, the output may indicate whether or not there is at least a 5% risk of the patient being above an unacceptable limit in any of the dimensions. In one embodiment, a statistical measure of the probability that a patient has certain visual symptoms may be provided (e.g., there is a 40% risk the patient has an unacceptable amount of glare). The measure may comprise a statistical measure, a quantitative score, or other form of measure. The measure may comprise a final, composite complaint score. In one embodiment, the measure may correspond to the format of output provided by questionnaires. In one embodiment, the output may comprise a recommendation of whether the patient should get a multifocal intraocular lens, as the tolerance to halos of the patient may be determined prior to surgery.

In one embodiment, the system may be configured to select a lens, such as an intraocular lens (including a multifocal intraocular lens) for implantation in the patient based on the testing result.

Figure 5:
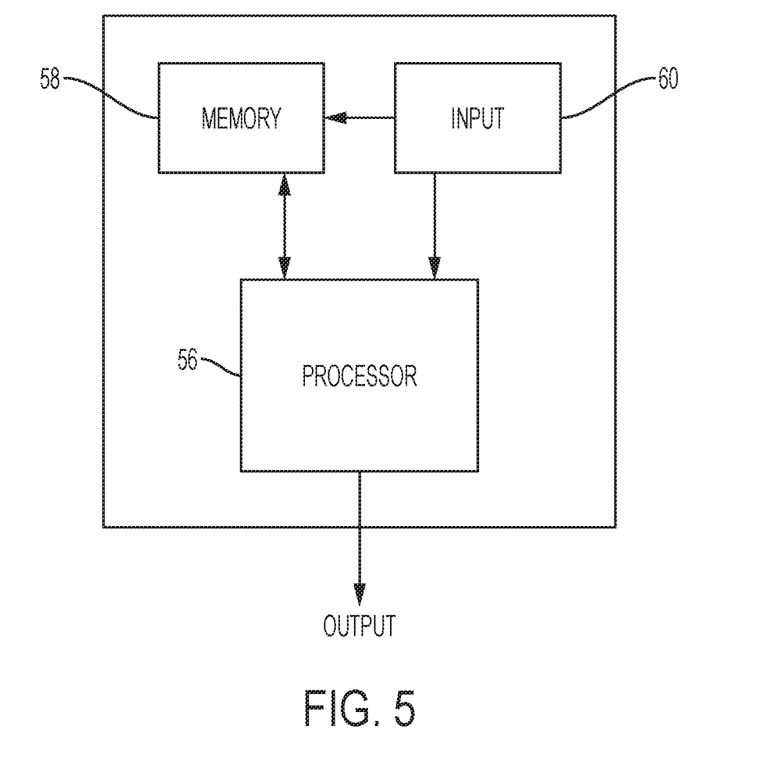
FIG. 5 illustrates a processor, memory, and input according to an embodiment of the present disclosure.

FIG. 5 illustrates a processor 56, a memory 58, and an input 60. The processor 56 may be configured to perform the determinations, including the calculations, of the disclosed method, and may be configured to perform the other steps disclosed herein. The memory 58 may be configured to store data for use by the processor 56. For example, the memory 58 may store the predetermined probability distribution functions for use as the initial probabilities. The memory 58 may also store the math necessary to calculate optical stimuli presentation, which may be done using pre-calculated matrixes (potentially several gigabytes in size) to speed up calculation.

The memory 58 may be configured to store a listing of lenses, such as intraocular lenses (including multifocal intraocular lenses), and the processor 56 may be configured to select one or more of the lenses from the memory 58 for implantation in the patient based on the testing results.

The input 60 may comprise an interface with an input device disclosed herein, and may provide information from the input device to the processor 56 and/or memory 58.

The system and apparatuses utilized to perform the methods disclosed herein may be varied as desired. In one embodiment, the system may be connected to a server or cloud based solutions. A server or cloud based solution may provide higher granularity than would be available with a personal computer. In one embodiment, the processor 56 may be positioned remotely from the input device and the display. For example, a patient may provide input with a mobile device (e.g., by making selections on a touchscreen of the mobile device such as a mobile phone or "smartphone") and the processor 56 may remotely perform the processes disclosed herein.

The methods disclosed herein may beneficially enhance the sensitivity and efficiency of visual symptom testing. The Bayesian method may be beneficially utilized to determine a measure of visual symptoms based on the patient's responses.

The methods disclosed herein may, in one embodiment, be based on a single stimulus response. In other embodiments and as disclosed herein, a greater number of stimuli responses may be utilized.

The methods disclosed herein may be utilized to measure visual symptoms of an individual having an intraocular lens (which may be monofocal or multifocal). In one embodiment, the methods disclosed herein may be used for other optical conditions, such as cataracts. The methods disclosed herein may be used as a first step to identify patients suffering from cataracts without losses in visual acuity. In testing for cataracts, the visual symptom parameters disclosed above may be tested. A correlation between the visual symptom parameters and a probability of cataracts may be known, and it may be determined whether the patient would benefit from cataracts surgery (e.g, because the patient scored highly for halos, or another visual symptom that is associated with cataracts).

In one embodiment, patients that are not indicating any visual symptoms may be tested. The tests may determine if the patient has a visual disturbance experience even though the patient does not report any visual symptoms.

In one embodiment, other psychophysical methods may be utilized with the system disclosed herein. A method of limits, a method of adjustment, a staircase procedure, an adaptive procedure, or QUEST or PEST methods may be utilized to construct a multi-dimensional threshold for the various parameters of interest (e.g., size, intensity).

The processor 56 disclosed herein may be utilized to perform or automate the processes disclosed herein. The processor 56 may include computer hardware and/or software, which may include one or more programmable processor units running machine readable program instructions or code for implementing some or all of one or more of the methods described herein. In one embodiment, the code is embodied in a tangible media such as a memory (optically a read only memory, a random access memory, a non-volatile memory, or the like) and/or a recording media (such as a floppy disk, a hard drive, a CD, a DVD, a memory stick, or the like). The code and/or associated data and signals may also be transmitted to or from the processor 56 via a network connection (such as a wireless network, an Ethernet, an internet, an intranet, or the like), and some or all of the code may also be transmitted between components of the system and within the processor 56 via one or more bus, and appropriate standard or proprietary communications cards, connector, cables, and the like can be included in the processor 56.

The processor 56 is preferably configured to perform the calculations and signal transmission steps described herein at least in part by programming the processor 56 with the software code, which may be written as a single program, a series of separate subroutines or related programs, or the like. The processor 56 may include standard or proprietary digital and/or analog signal processor hardware, software, and/or firmware, and has sufficient processing power to perform the calculations described herein. The processor 56 optionally includes a personal computer, a notebook computer, a tablet computer, a proprietary processing unit, or a combination thereof. Standard or proprietary input devices (such as a mouse, keyboard, touchscreen, joystick, etc.) and output devices (such as a printer, speakers, display screen, etc.) associated with computer systems may also be included in the system, and additional processors having a plurality of processing units (or even separate computers) may be employed in a wide range of centralized or distributed data processing architectures.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of systems, apparatuses, and methods as disclosed herein, which is defined solely by the claims. Accordingly, the systems, apparatuses, and methods are not limited to that precisely as shown and described.

Certain embodiments of systems, apparatuses, and methods are described herein, including the best mode known to the inventors for carrying out the same. Of course, variations on these described embodiments will become apparent to those of ordinary skill in the art upon reading the foregoing description. The inventor expects skilled artisans to employ such variations as appropriate, and the inventors intend for the systems, apparatuses, and methods to be practiced otherwise than specifically described herein. Accordingly, the systems, apparatuses, and methods include all modifications and equivalents of the subject matter recited in the claims appended hereto as permitted by applicable law. Moreover, any combination of the above-described embodiments in all possible variations thereof is encompassed by the systems, apparatuses, and methods unless otherwise indicated herein or otherwise clearly contradicted by context.

Groupings of alternative embodiments, elements, or steps of the systems, apparatuses, and methods are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses an approximation that may vary. The terms "approximate[ly]" and "substantial[ly]" represent an amount that may vary from the stated amount, yet is capable of performing the desired operation or process discussed herein.

The terms "a," "an," "the" and similar referents used in the context of describing the systems, apparatuses, and methods (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the systems, apparatuses, and methods and does not pose a limitation on the scope of the systems, apparatuses, and methods otherwise claimed. No language in the present specification should be construed as indicating any non-claimed element essential to the practice of the systems, apparatuses, and methods.

All patents, patent publications, and other publications referenced and identified in the present specification are individually and expressly incorporated herein by reference in their entirety for the purpose of describing and disclosing, for example, the compositions and methodologies described in such publications that might be used in connection with the systems, apparatuses, and methods. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A method of determining visual symptoms of a patient, comprising:
   presenting, on a display screen, a first stimulus to the patient comprising a first image comprising an image of one or more of halo or glare having a first size, type, or intensity;
   receiving, on an input device, a first response to the first stimulus by the patient, the first response being a binary response and comprising an indication by the patient of whether the patient's visual symptoms are better or worse than the one or more of halo or glare having the first size, type, or intensity of the first image;
   determining, using a processor, a second image based on the first response, the second image comprising an image of one or more of halo or glare having a halo or a glare that is less than the first size, type, or intensity of the one or more of halo or glare of the first image if the binary response indicates that the patient's visual symptoms are better than the one or more of halo or glare of the first image, or having a halo or a glare that is greater than the first size, type, or intensity of the one or more of halo or glare of the first image if the binary response indicates that the patient's visual symptoms are worse than the one or more of halo or glare of the first image;
   presenting, on the display screen, a second stimulus to the patient comprising the second image;
   receiving, on the input device, a second response to the second stimulus by the patient, the second response being a binary response and comprising an indication by the patient of whether the patient's visual symptoms are better or worse than the one or more of halo or glare of the second image;
   updating, using the processor, a prior probability of visual symptoms for the patient based on the first response or the second response;
   determining, using the processor, a quantitative measure of visual symptoms of the patient based on the updated prior probability; and
   selecting a lens for implantation in the patient based on the determined quantitative measure of visual symptoms.

2. The method of claim 1, wherein the image of one or more of halo or glare of the first image comprises one or more of halo or glare of an intraocular lens.

3. The method of claim 1, wherein the prior probability is based on a prior response by the patient to a prior stimulus presented to the patient.

4. The method of claim 1, wherein the prior probability is based on a plurality of prior responses by the patient to a plurality of prior stimuli presented to the patient.

5. The method of claim 1, wherein updating the prior probability of visual symptoms for the patient based on the first response or the second response includes utilizing a Bayesian method.

6. The method of claim 1, wherein determining the quantitative measure of the visual symptoms of the patient includes determining whether the visual symptoms of the patient exceed a threshold.

7. The method of claim 1, further comprising selecting, using the processor, a multifocal intraocular lens for implantation in the patient based on the quantitative measure of visual symptoms of the patient.

8. The method of claim 1, wherein the prior probability is an initial probability based on whether the patient belongs to certain demographic groups.

\* \* \* \* \*